United States Patent [19]

Utsunomiya et al.

[11] Patent Number: 4,690,151

[45] Date of Patent: Sep. 1, 1987

[54] BLOOD PRESSURE MEASURING APPARATUS

[75] Inventors: Shunji Utsunomiya, Kyoto; Tsutomu Teramoto, Takatsuki; Tadashi Huruta, Ohtsu, all of Japan

[73] Assignee: Omron Tateisi Electronics Co., Kyoto, Japan

[21] Appl. No.: 800,963

[22] Filed: Nov. 22, 1985

[30] Foreign Application Priority Data

Nov. 22, 1984 [JP] Japan ................... 59-247340

[51] Int. Cl.$^4$ .............................................. A61B 5/02
[52] U.S. Cl. ..................................... 128/682; 128/683
[58] Field of Search ............... 128/672, 677, 680–683; 381/51, 53

[56] References Cited

U.S. PATENT DOCUMENTS

| | | | |
|---|---|---|---|
| 4,141,350 | 2/1979 | Shinoda | 128/680 |
| 4,273,136 | 6/1981 | Kubo et al. | 128/681 X |
| 4,321,929 | 3/1982 | Lemelson et al. | 128/680 X |
| 4,325,383 | 4/1982 | Lacks | 128/677 |
| 4,397,317 | 8/1983 | Villa-Real | 128/680 |
| 4,469,099 | 9/1984 | McEwen | 128/682 X |
| 4,510,942 | 4/1985 | Miyamae et al. | 128/680 |
| 4,558,707 | 12/1985 | Miyamae et al. | 128/683 |

*Primary Examiner*—Henry J. Recla
*Assistant Examiner*—Angela D. Sykes

*Attorney, Agent, or Firm*—Schwartz, Jeffery, Schwaab, Mack, Blumenthal & Evans

[57] ABSTRACT

A blood pressure measuring apparatus for measuring maximum and minimum values of blood pressure comprises a bag-like arm belt for compressing an arm of a person whose blood pressure is to be measured, a power source switch, pressurizing pump for pressurizing interiorly the bag-like belt, pressure sensor for detecting pressure within the bag-like belt, K's sound sensor for detecting blood information by decreasing the pressure within the bag-like belt, blood pressure determining computer for determining maximum and minimum values of the blood pressure on the basis of output signals of the pressure sensor and the K's sound sensor, pressure value change-over switch for setting a pressure value to be established within the bag-like belt, pressure increasing pump for increasing the pressure within the bag-like belt to the set pressure value, an announcer for announcing the set pressure value in the form of speech information upon closing of the power source switch, to thereby inform the set pressure value in the form of speech before the pressurizing operation is initiated. Every time when the set pressure value is renewed by the pressure value change-over switch, the speech information announcer can inform user of the renewed value of the set pressure. Information of the set pressure value can thus be positively made available before performing the blood pressure measurement, whereby erroneous measurement is prevented.

2 Claims, 4 Drawing Figures

BLOOD PRESSURE MEASURING APPARATUS

BACKGROUND OF THE INVENTION

1. Field of the Invention

The present invention relates generally to a blood pressure measuring apparatus, and more particularly to the blood pressure measuring apparatus of the type in which a bag-like belt or band wound around an arm of a person is automatically pressurized.

2. Description of the Prior Art

Heretofore, there is known a blood pressure measuring apparatus in which the bag-like belt or band attached to a person whose blood pressure is to be measured is pressurized by means of a pressurizing pump, and subsequently the pressure within the bag-like band is detected by means of a pressure sensor while the pressure within the band is concurrently decreased at a reduced rate through a show discharge value. On the other hand, the Korotokov's sound (hereinafter, also referred to simply as K's sound) is detected by using a K's sound sensor. The output signals of both sensors are processed by a microcomputer to derive the maximum and minimum values of the blood pressure which are then visually displayed.

In the blood measuring apparatus of the type described above, it is known that the pressurization of the bag-like belt or band is performed automatically up to a preset pressure value or level. The pressure value must of course be higher than the expected maximum pressure value as measured. It is also empirically known that when the set pressure value is excessively high, difficulty may be encountered in attaching the accurate measurement.

However, the maximum blood pressure becomes different in dependence on the individuals whose blood pressures are to be measured. Correspondingly, the present pressure level must be correspondingly different. Accordingly, in case the setting of the pressure level before the measurement is forgotten or confirmation of the set pressure level is left neglected before the pressurization, there may happen such situation in which the pressurization of the arm compressing belt is insufficient for measuring the blood pressure of a given person with an acceptable accuracy. In that case, the compressed air within the bag-like belt must be discharged once and the pressurization has to be again performed. In the hitherto known blood pressure measuring apparatus, the set pressure value preset by the pressure setting device is simply displayed in the form of numerals or marks, involving thus a problem that the set pressure valve is left unconfirmed or not altered to a proper set value.

SUMMARY OF THE INVENTION

An object of the present invention is to provide a blood pressure measuring apparatus which is capable of performing automatically measurement of the blood pressure and which allows operator or user to confirm previously the preset pressure value or level without fail.

Another object of the present invention is to provide a blood pressure measuring apparatus which can announce beforehand the preset value for the pressurization in the form of speech or voice information to thereby allow the operator or user to confirm whether or not the preset pressure is of a proper value.

A further object of the invention is to provide a blood pressure measuring apparatus in which the level for the pressurization can be properly preset by virtue of the speech or voice information of the updated preset pressure level every time the set pressure level is altered or changed.

In view of the above objects, there is provided according to an aspect of the invention a blood pressure measuring apparatus which is equipped with pressure level or value setting means for setting a pressure level to be established within a bag-like arm belt or band, pressure increasing means for increasing the pressure within the bag-like belt to the pressure level set by the pressure level setting means, and information means for announcing the set pressure value in the form of speech in response to the closing of a power source switch.

With such arrangement of the blood pressure measuring apparatus, the set pressure value is announced as the voice information in response to the closing of the power source switch. Accordingly, an operator or user can perform the arm belt-pressurizing operation only after the confirmation of the set pressure value. Consequently, erroneous measurement can be positively excluded.

In a preferred embodiment of the present invention, the speech information means can be imparted with a function for announcing the updated set pressure value upon every alteration of the preset pressure level, whereby any updated set pressure level is informed to the operator or user before he or she performs the blood pressure measurement.

In summary, the blood pressure measuring apparatus which is so arranged that the pressure level set for the pressurization of the bag-like arm belt and/or any updated set pressure level is announced to the operator or user before initiation of the pressurization of the bag-like band allows the operator or user to confirm the currently set pressure level for the pressurization without fail, whereby the blood pressure measurement can be easily performed accurately and properly to the individuals.

By virtue of the information of the set pressure value or level, the pressure setting device such as slide switch may be implemented in a reduced size because displacement of the slide switch for setting the pressure levels may be small. Besides, the pressure setting device may be constituted by a push button switch or touch switch.

Further, because of no necessity of visually confirming the set pressure value, the measuring procedure can be facilitated. Besides, inadvertent manipulation will not result in erroneous result of measurement by virtue of the aforementioned speech information facility.

Moreover, because the pressure information is given in the form of voice or speech, even a blind person can confirm the set pressure level, facilitating thus the blood pressure measurement.

The above and other objects, features and advantages of the invention will be more apparent upon consideration of the following description of the preferred embodiment. The description refers to the drawings.

DESCRIPTION OF THE PREFERRED EMBODIMENTS

In the following, the invention will be described in detail in conjunction with exemplary embodiments thereof by referring to the accompanying drawings.

Figure 1:
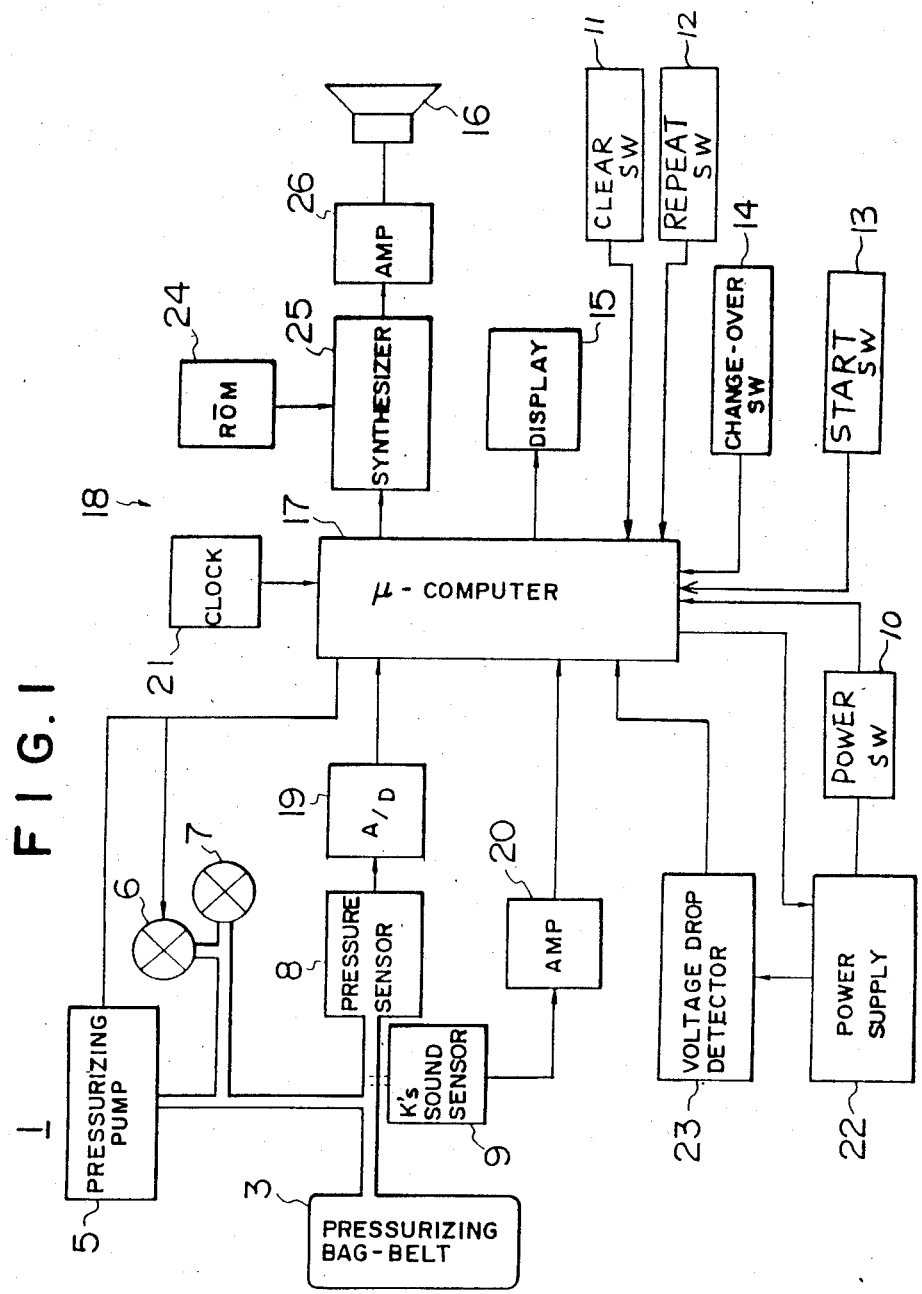
FIG. 1 is a block diagram showing a general arrangement of a blood pressure measuring apparatus according to an exemplary embodiment of the present invention.
Figure 2:
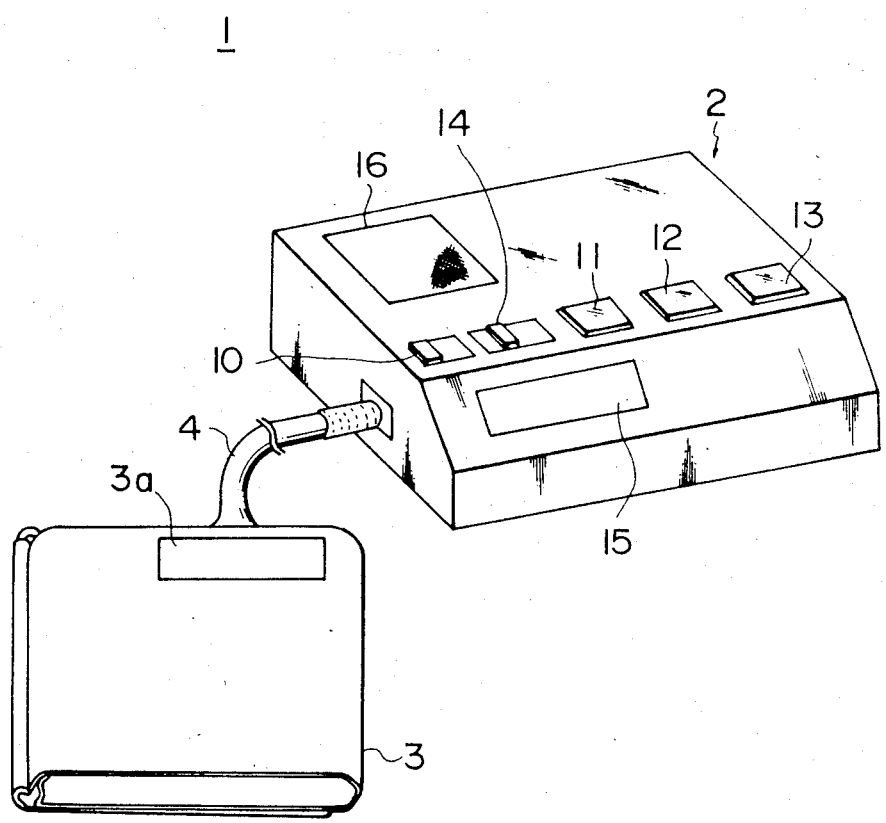
FIG. 2 is a perspective view of a blood pressure measuring apparatus to which the present invention is applied.

Referring to the drawings and particularly to FIGS. 1 and 2, a reference numeral 1 denotes generally a blood pressure measuring apparatus adapted to measuring maximum and minimum values of the blood pressure at times corresponding respectively to occurrence and disappearance of Korotokov's sound (also referred to simply as K's sound). The blood pressure measuring apparatus comprises a main body 2 incorporating various functional units and a display, and a bag-like arm belt or band 3 connected to the main body through a flexible tube 4 and adapted to be wound around an arm of a person whose blood pressure is to be measured, wherein the apparatus is so arranged that the bag-like arm belt or band 3 is automatically pressurized.

The bag-belt or band 3 is aerodynamically coupled to a rapid discharge valve 6 and a slow discharge valve 7. It will be seen that the hollow interior of the bag-like band 3 is pressurized by driving the pressurizing pump 5 to thereby obstruct blood flow in the arm. Further, the bag-like band 3 is provided with a pressure sensor (pressure detecting means) 8 and K's sound sensor (information detecting means)9. The pressure sensor 8 serves to detect the pressure within the baglike band 3, while the K's sound sensor 9 serves the detect the Korotokov's sound representative of blood pressure information. A reference symbol 3a denotes a ribbon adapted to mount the K's sound sensor 9.

The main body 2 includes a power source switch 10, a clear switch 11, a repeat switch 12, a start switch 13, a set pressure value change-over switch 14, a display field 15, a speaker 16 and a blood pressure information deriving means 18 which may be constituted by a microcomputer 17 and others.

Upon actuation of the start switch 13 (FIG. 2) which serves also as a step switch, as will be described hereinafter, the microcomputer 17 produces an activation signal to the pressurizing pump 5 to thereby allow the bag-like arm belt 3 to be automatically pressurized with the rapid discharge valve 6 being closed. The detection signal produced by the pressure sensor 8 is supplied to the microcomputer by way of an analogue-to-digital (A/D) converter 19, while the detection signal outputted from the K's sound sensor 9 is inputted to the microcomputer 17 through an amplifier 20. The microcomputer 17 is further supplied with a clock signal from a clock circuit 21 and operates to arithmetically determine the maximum blood pressure value and the minimum pressure value on the basis of the detection signals as inputted.

The microcomputer 17 is supplied with an electric power from a power supply source 22 upon closing of the power source switch 10. A voltage-drop detecting circuit 23 is additionally connected to the power supply source 22. In response to the output signal produced by the voltage-drop detecting circuit 23, the microcomputer 17 interrupts the power supply from the source circuit 22.

The set pressure value change-over switch (pressure setting means) 14 may be constructed, for example, by a slide switch (which can set selectively four levels of pressure, e.g. 150 mmHg, 175 mmHg, 200 mmHg, 225 mmHg). The microcomputer 17 drives the pressurizing pump 5 on the basis of the signal produced by this switch 14 to thereby pressurize the interior of the bag-like belt or band 3 up to the pressure level currently set by the switch 14.

The display 15 serves to display the maximum and minimum values of the blood pressure in accordance with the signal supplied from the microcomputer 17.

Further, sound information corresponding to the data produced by the microcomputer 17 and stored in a ROM 24 is outputted through a synthesizer 25 and an amplifier 26 to be produced as speech information from the loud speaker 16, whereby the set pressure value or level is announced in the form of speech or voice information.

Figure 3:
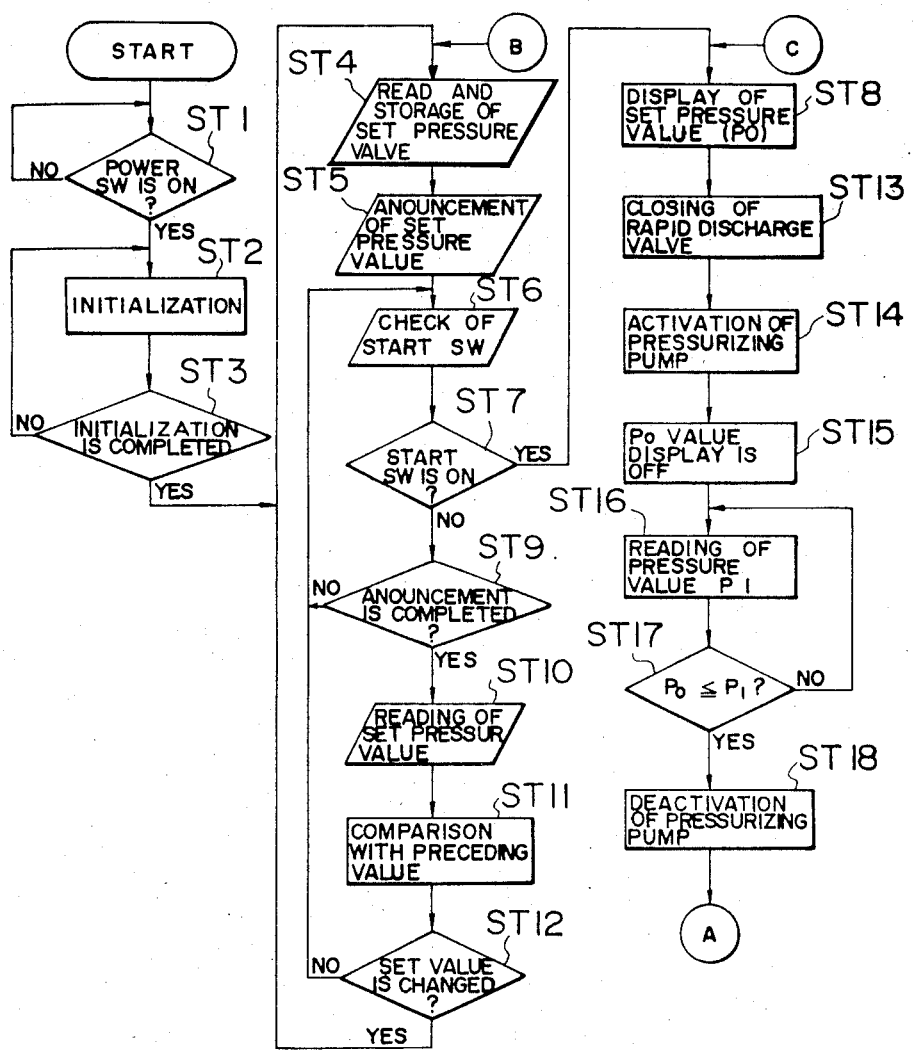
FIGS. 3 and 4 are flow charts for illustrating operations of the blood pressure measuring apparatus.
Figure 4:
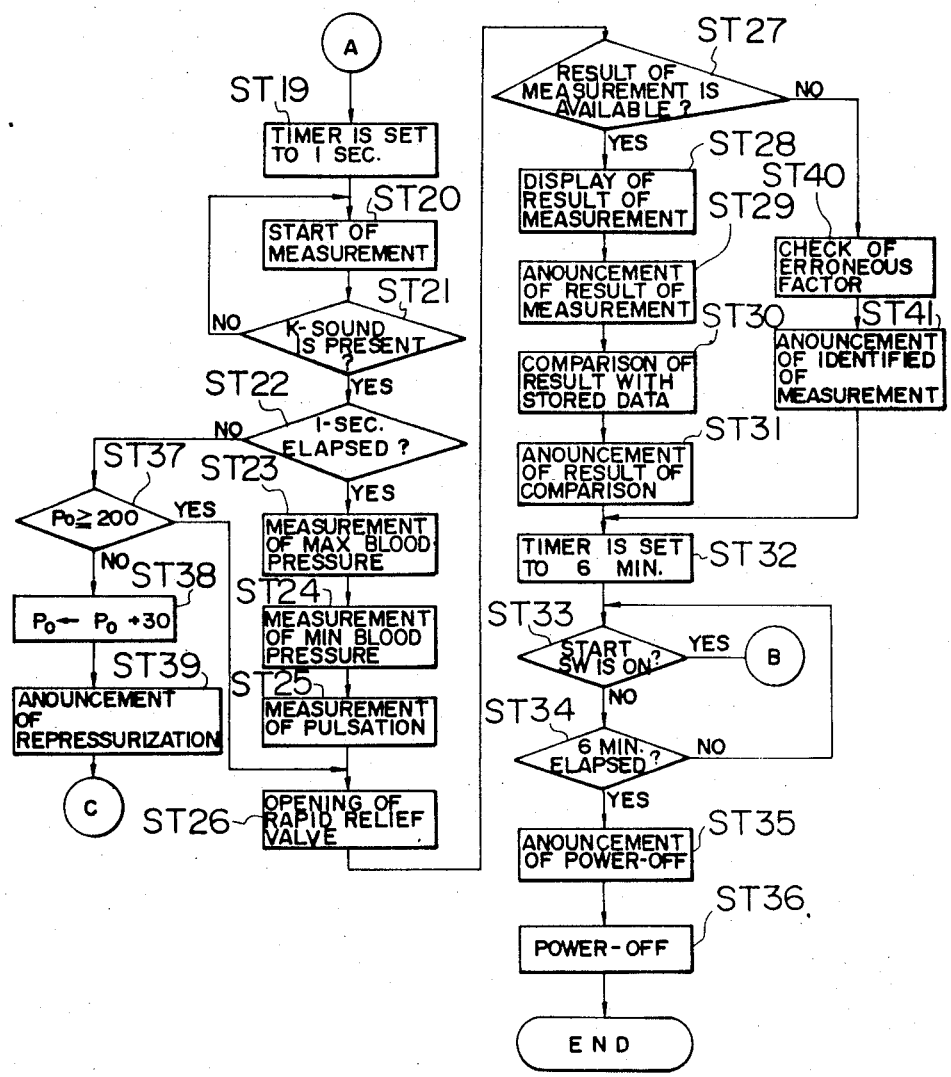

Next, arrangement and operation of the blood pressure measuring apparatus will be described by referring to flow charts shown in FIGS. 3 and 4.

At first, it is decided at a step 1 (denoted by ST1 in the figures with the same applying to other steps) whether the power source switch 10 is closed (ON) or not. When this switch 10 is closed, initialization is conducted at a step 2. It is then determined at a step 3 whether or not the initialization has been completed. If the result is negative (NO), the step 2 is regained. Otherwise, a step 4 is executed.

At the step 4, the set pressure value is fetched and stored. More specifically, the pressure value or level set at the pressure setting change-over switch 14 is read out and stored a memory incorporated in the microcomputer 17. At a step 5, the output signal of the microcomputer 17 is supplied to the synthesizer 25 whose output signal in turn is supplied to the speaker 16, whereby the information of the set pressure value such as "175 mmHg" is announced in the form of speech.

Subsequently, at a step 6, the state of the start switch 13 is checked to determine whether the switch 13 is closed (ON) or opened (OFF) at a step 7. In case the switch 13 is closed, the set pressure value $P_O$ is displayed at the display field 15 at a step 8. Otherwise, it is checked at a step 9 whether or not the set pressure value was announced. If the result of the step 9 is negative (NO), the step 6 is regained to repeat the operation mentioned above. On the other hand, when the announcement was made (YES), the set pressure value is fetched again at a step 10. At a next step 11, this value is compared with the set value already read at the step 4. Then, at a step 12, it is decided whether or not the set pressure value is changed on the basis of the result of comparison.

In this manner, it is possible for the user to confirm whether or not the set pressure value is proper on the basis of the announced information produced at the step 5. In case the value is not proper, the set pressure can be altered to the proper value by correspondingly manipulating the change-over switch 14 before the start switch 13 is turned on or before the pressurizing pump 5 is driven.

When it is determined at the step 12 that the set pressure value is not changed, the step 6 is regained, being followed by the execution mentioned above. Otherwise, the step 4 is regained, whereby the updated pressure value is announced at the step 5, and execution of the subsequent steps is repeated, as described above.

In case the set pressure is of a proper value, the start switch 13 is closed (resulting in "YES" of the decision step 7), the set pressure value $P_O$ is displayed (step 8) and the rapid discharge valve 6 is closed (step 13) while the pressurizing pump 5 is driven St 14) to pressurize internally the bag-like band 3. After the display of the set pressure value $P_O$ is reset at a step 15, the current pressure value $P_I$ within the bag-like band 3 is read out by making use of the detection signal produced by the pressure sensor 8 at a step 16, being followed by a step 17 where it is determined whether the set pressure value $P_o$ has been attained. At a standby step 16, attainment of the pressure within the band 3 to the set pressure value is awaited, whereupon the operation of the pressurizing pump 5 is stopped at a step 18.

Next, at a step 19, a timer (also incorporated in the microcomputer) is set to 1 (one) second to start the measurement by opening the slow discharge valve 7 (step 20). It is determined at a step 21 whether the K's sound is detected by the K's sound sensor 9. Upon detection of the K's sound, it is checked at a step 22 whether duration of one second set at the step 19 has elapsed or not. When the K's sound is detected after lapse of one second, measurement of the blood pressure at the normal pressurization is allowed. Accordingly, the maximum blood pressure value is measured at a step 23, while the minimum blood pressure value is measured at a step 24 with pulsation being measured at a step 25. The microcomputer 17 arithmetically determines the blood pressure values at the occurrence of the K's sound and at the termination thereof, respectively. Subsequently, the rapid discharge valve 6 is opened at a step 29 to depressurize the bag-like band 3.

Subsequently, it is decided at a step 27 whether the results of measurement has been derived. When the measurement has been performed in the manner described above, the result of the measurement, i.e. the maximum and minimum blood pressure values are displayed at the display field 15 at a step 28, while the same information is announced through the speaker 16 in the form of speech information (step 29). At a step 30, the result of the measurement is compared with the stored reference data, the result of which is announced through the speaker 16 at a step 31. More specifically, the result of measurement is compared with the data stored previously in a memory of the microcomputer 17 to ascertain whether the measured blood pressures are within the normal range or not. If abnormal, speech information is produced as to whether the measured blood pressure is high or low as compared with the normal or standard value.

Subsequently, the timer is set to a duration of six minutes at a step 32, being followed by a step 33 where it is checked whether the start switch 13 is turned on or not. If the start switch 13 is closed, the step 4 is regained to allow a new cycle of measurement to be started, whereby the process described above is repeated. On the other hand, unless the switch 13 is closed, it is determined whether the duration of six minutes has elapsed or not. At a step 33, the lapse of six minutes is waited for to thereby determine whether the start switch 13 is still closed. When the start switch 13 is found opened, speech information to the effect that the power supply is turned off is issued through the speaker 16 at a step 35, being followed by a step 36 where the power supply is turned off to prevent useless power consumption. The measuring process then comes to an end.

On the other hand, when K's sound is detected before one second has elapsed, this means an abnormal pressurization. Accordingly, the decision step 22 results in "NO", and it is determined at the step 37 whether or not the set pressure value $P_O$ is higher than 200 mmHg. When the set pressure $P_O$ is lower than 200 mmHg, then 30 mmHg is added thereto (step 38), and repressurization is announced through the speaker 16 (step 39). After the step 8 is regained, the pressurizing pump 5 is activated to repeat the process or operation described above to continue the blood pressure measurement.

When it is found at the step 37 that the set value is higher than 200 mmHg, the rapid discharge valve 6 is opened at a step 26. At this time, the result of measurement is not obtained at the step 27. Accordingly, the result of the step 27 is "NO". In that case, the cause or erroneous factors involved is checked (step 40) and announced through the speaker at a step 41. Subsequently, the step 32 is regained to repeat the process described above.

The illustrated embodiment is adapted to measure the blood pressure by meking use of K's sound. It should however be understood that the invention can be applied to the measurement of blood pressure with the aid of the information detecting means adapted to detect pulsation.

Further, the pressurizing means is not restricted to the pressurizing pump 5.

Of course, the pressure setting means is not restricted to the slide change-over switch 14.

In the foregoing, the invention has been described in conjunction with the preferred embodiment. However, it is obvious that numerous modifications and variations may readily occur to those skilled in the art without departing from the spirit and scope of the invention.

What is claimed is:

1. In a blood pressure measuring apparatus for measuring maximum and minimum values of blood pressure, comprising a bag-like arm belt for compressing an arm of a person whose blood pressure is to be measured, a power source switch, pressurizing means for pressurizing interiorly said bag-like belt, pressure detecting means for detecting pressure within said bag-like belt, information detecting means for detecting blood information in the course of decreasing of the pressure within said bag-like belt, blood pressure determining means for determining maximum and minimum values of the blood pressure on the basis of output signals of said pressure detecting means and said information detecting means, a combination comprising; pressure setting means for setting a pressure value to be established within said bag-like belt, pressure increasing means for increasing the pressure within said bag-like belt to said set pressure value, announcing means for announcing said set pressure value in the form of speech information upon closing of said power source switch, to thereby issue said set pressure value in the form of speech information, before the pressurizing operation is effected.

2. A blood pressure measuring apparatus according to claim 1, said announcing means includes means for additionally providing an updated set pressure value when said set pressure value is renewed by said pressure setting means.

* * * * *